United States Patent
Hamilton et al.

(10) Patent No.: US 6,368,301 B1
(45) Date of Patent: *Apr. 9, 2002

(54) CATHETER HAVING A SOFT DISTAL TIP

(75) Inventors: Rasean L. Hamilton, Santa Clara; Teresita R. Baerga, San Jose, both of CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/471,053

(22) Filed: Dec. 21, 1999

(51) Int. Cl.$^7$ .............................................. A61M 29/00
(52) U.S. Cl. ..................................... 604/103; 604/96.01
(58) Field of Search ............................... 604/96.01, 103, 604/915, 523, 921, 525, 103.05, 103.06; 606/192, 194

(56) References Cited

U.S. PATENT DOCUMENTS

| | | | |
|---|---|---|---|
| 3,832,253 A | 8/1974 | Di Palma et al. .............. 156/86 |
| 3,865,666 A | 2/1975 | Shoney ........................ 156/245 |
| 3,884,242 A | 5/1975 | Bazell et al. ................ 128/351 |
| 4,157,094 A | 6/1979 | Patel ........................... 128/349 |
| 4,276,874 A | 7/1981 | Wolvek et al. ................. 128/1 |
| 4,385,635 A | 5/1983 | Ruiz ........................... 128/658 |
| 4,413,989 A | 11/1983 | Schjeidahl et al. ........... 604/96 |
| 4,496,345 A | 1/1985 | Hassoon ..................... 604/103 |
| 4,540,404 A | 9/1985 | Wolvek ........................ 604/96 |
| 4,702,252 A * | 10/1987 | Brooks et al. |
| 4,706,670 A | 11/1987 | Andersen et al. ............ 128/344 |
| 4,782,834 A | 11/1988 | Maguire et al. ............. 128/344 |
| 4,917,667 A | 4/1990 | Jackson ........................ 604/96 |
| 4,921,483 A * | 5/1990 | Wijay et al. |
| 5,078,072 A | 1/1992 | Pomeranz ................... 604/280 |
| 5,171,232 A | 12/1992 | Castillo et al. ............. 604/280 |
| 5,234,416 A * | 8/1993 | Macauley et al. |
| 5,250,069 A | 10/1993 | Nobuyoshi et al. ......... 606/192 |
| 5,267,959 A | 12/1993 | Forman ....................... 604/103 |
| 5,366,442 A * | 11/1994 | Wang et al. |
| 5,425,712 A | 6/1995 | Goodin ......................... 604/96 |
| 5,697,906 A | 12/1997 | Ariola et al. .................. 604/96 |
| 5,728,063 A | 3/1998 | Preissman et al. ............ 604/96 |
| 5,728,065 A | 3/1998 | Follmer et al. ................ 604/96 |
| 5,762,637 A | 6/1998 | Berg et al. ................... 604/264 |
| 5,769,819 A | 6/1998 | Schwab et al. .............. 604/103 |
| 5,769,830 A * | 6/1998 | Parker |
| 5,827,225 A | 10/1998 | Ma Schwab ................. 604/96 |
| 5,843,090 A | 12/1998 | Schuetz ....................... 606/108 |
| 5,891,110 A * | 4/1999 | Larson et al. |

FOREIGN PATENT DOCUMENTS

| | | |
|---|---|---|
| DE | 3900635 A1 | 1/1989 |
| EP | 0517075 A1 | 5/1992 |
| GB | 2337094 A | 4/1999 |
| WO | WO 99/44666 | 2/1999 |

* cited by examiner

Primary Examiner—Richard K. Seidel
Assistant Examiner—LoAn H. Thanh
(74) Attorney, Agent, or Firm—Coudert Brothers LLP

(57) ABSTRACT

An intraluminal catheter comprising an elongated catheter shaft having proximal and distal ends and at least one lumen, and a tip member on a distal end of the catheter having a proximal end spaced distally apart from the distal end of the catheter shaft.

14 Claims, 3 Drawing Sheets

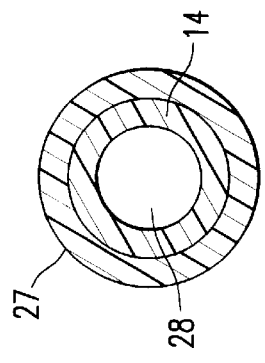
FIG. 3
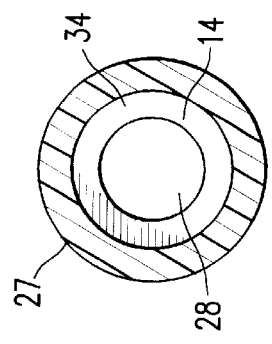
FIG. 4
FIG. 5
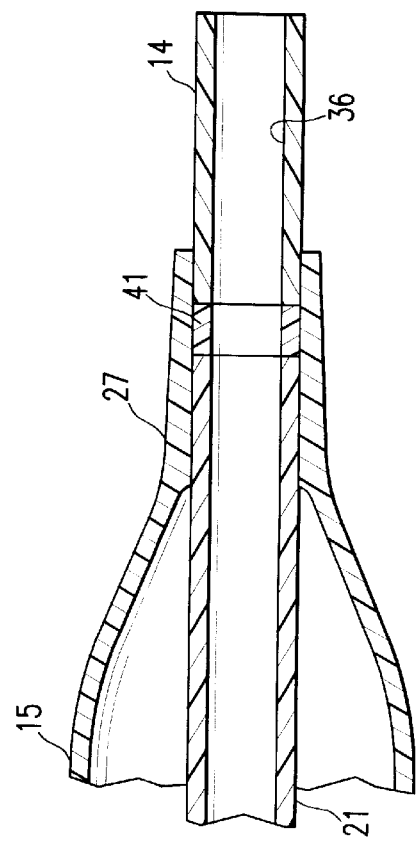
FIG. 6
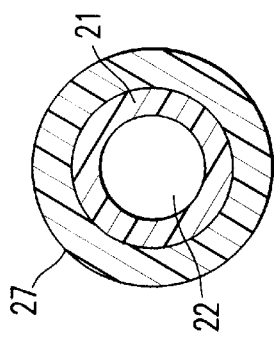
FIG. 7

CATHETER HAVING A SOFT DISTAL TIP

BACKGROUND OF THE INVENTION

This invention relates to the field of medical devices, and more particularly to a balloon catheter having a soft distal tip.

Catheters designed for intravascular procedures such as angioplasty have a number of design considerations. Such catheters must be able to transmit force along the length of the catheter shaft so that the catheter can be pushed through the patient's vasculature. However, the catheter shaft must also have sufficient flexibility to allow it to track over a guidewire through tortuous vasculature. The catheter also must be able to cross stenosed portions of the vascular anatomy.

Prior art intravascular catheters have commonly included a soft distal tip to prevent or minimize injury to the vessel during advancement of the catheter therein. One difficulty has been forming a connection between the soft tip and the catheter which is sufficiently strong to prevent disengagement of the soft tip or kinking at the junction between the soft tip and catheter shaft. Additionally, it is necessary to balance the strength of the connection between the soft tip and the catheter shaft with the need to minimize the stiffness of the distal end of the catheter. Minimizing the stiffness of the distal end of the catheter results in improved maneuverability of the catheter.

Accordingly, it would be a significant advance to provide a catheter with a soft tip having improved performance. This invention satisfies these and other needs.

SUMMARY OF THE INVENTION

The invention is directed to an intraluminal catheter having a soft distal tip, and generally comprising an elongated catheter shaft having proximal and distal ends, at least one lumen, and a soft distal tip member secured to the distal end of the catheter having a proximal end spaced distally apart from the distal end of the catheter shaft.

One embodiment of the invention is a balloon catheter generally comprising an elongated catheter shaft having an inflation lumen therein, a balloon on a distal shaft section in fluid communication with the inflation lumen, and a soft distal tip member on a distal end of the catheter. In accordance with the invention, the tip member has a proximal end spaced distally apart from the distal end of the catheter shaft. In one presently preferred embodiment, a distal shaft section of the balloon is bonded to the distal end of the catheter shaft, so that the balloon inflatable interior is spaced proximal to the distal end of the elongated catheter shaft. The balloon distal shaft section is also bonded to the proximal end of the tip member, to thereby secure the tip member to the distal end of the catheter. The tip member typically has a lumen in fluid communication with a lumen of the catheter distal shaft section.

The distal tip member is preferably softer than the catheter shaft, to provide improved catheter maneuverability and decrease the risk of damage to the patient's vessel during advancement of the catheter therein. The tip member is typically formed of a polymeric material having a Shore Durometer hardness which is lower than the Shore Durometer hardness of the polymeric material forming at least a section of the catheter shaft. The Shore Durometer hardness of the polymeric material forming the tip member is about 35D to about 63D, preferably about 40D to about 55D. In a presently preferred embodiment, the tip member is formed of a polyether block amide polymer such as PEBAX (available from Autochem). However, the tip member may be formed of a variety of suitable materials, including polyolefin based copolymers such as a polyethylene based adhesive polymers such as an ethylene-acrylic acid copolymer which is sold commercially as PRIMACOR by Dow Chemical Co., and polyurethanes, such as polyurethane block copolymers such as PELLETHANE (a polyester based polyurethane, available from Dow Plastics).

In accordance with the invention, the tip member has a proximal end spaced distally apart from the distal end of the catheter shaft. In one embodiment, a gap exists between the distal end of the shaft and the proximal end of the tip member, and the balloon distal shaft section surrounds and extends over the gap. In another embodiment, a portion of the balloon distal shaft section or an intermediate member is disposed within the space between the distal end of the catheter shaft and the proximal end of the tip member.

A method of forming a distal tip of the invention generally comprises positioning a proximal end of the tip member within a balloon distal shaft section, so that the tip member proximal end is spaced distally apart from a distal end of a catheter shaft which is also within the balloon distal shaft section, and fusion bonding the balloon distal shaft section of the catheter shaft and the tip member. In one embodiment, the balloon material flows during fusion bonding into at least a part of the space between the proximal end of the catheter shaft and the distal end of the tip member.

The catheter of the invention having a distal tip member spaced distally from the distal end of the catheter shaft has excellent crossability and trackability. The catheter has a smooth transition in stiffness along the distal end of the catheter at the distal tip member, to improve handling and performance and minimize kinking. Additionally, the catheter has good tensile strength at the tip member attachment, without disadvantageously increasing the stiffness or profile of the distal end of the catheter. These and other advantages of the invention will become more apparent from the following detailed description and exemplary drawings.

BRIEF DESCRIPTION OF THE DRAWINGS

FIG. 3 is a cross sectional view of the catheter shown in FIG. 2, taken along lines 3—3.

FIG. 4 is a cross sectional view of the catheter shown in FIG. 2, taken along lines 4—4.

FIG. 5 is a cross sectional view of the catheter shown in FIG. 2, taken along lines 5—5.

FIG. 6 is an enlarged, longitudinal cross sectional view of an alternate embodiment of the catheter of the invention, having balloon shaft material between the catheter shaft and tip member.

FIG. 7 is an enlarged, longitudinal cross sectional view of an alternate embodiment of the catheter of the invention, having an intermediate member between the catheter shaft and distal tip member.

DETAILED DESCRIPTION OF THE INVENTION

Figure 1:
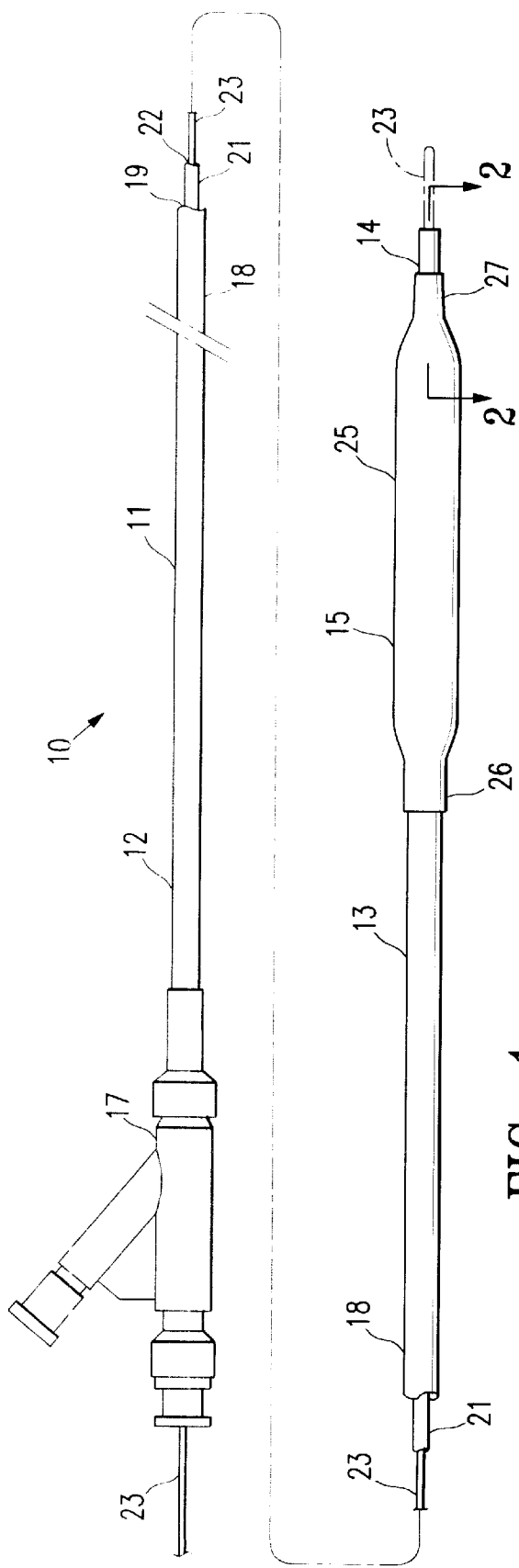
FIG. 1 is an elevational view of a balloon catheter which embodies features of the invention.

FIG. 1 illustrates a balloon catheter 10 embodying features of the invention, comprising an elongated catheter shaft 11 having a proximal shaft section 12 and a distal shaft section 13, a tip member 14, an inflatable balloon 15 on the distal catheter shaft section 13 having an interior 16, and an adapter 17 on the proximal catheter shaft section 12. In the embodiment illustrated in FIG. 1, the catheter shaft 11 comprises an outer tubular member 18 having an inflation lumen 19, and an inner tubular member 21 having a guidewire receiving lumen 22 disposed within the outer tubublar member. Guidewire 23, illustrated in FIG. 1 within guidewire receiving lumen 22, extends to port 24 in the distal end of the tip member 14. Balloon 15 has a working section 25, a proximal shaft section 26 disposed about and secured to a distal portion of the outer tubular member 18, and a distal shaft section 27.

Figure 2:
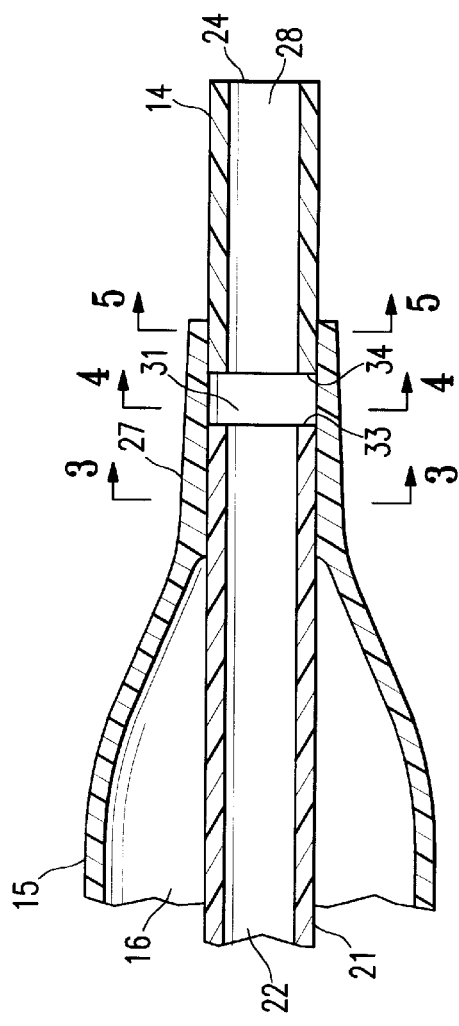
FIG. 2 is an enlarged, longitudinal cross sectional view of the distal end of the catheter shown in FIG. 1, taken along lines 2—2.
Figure 8:
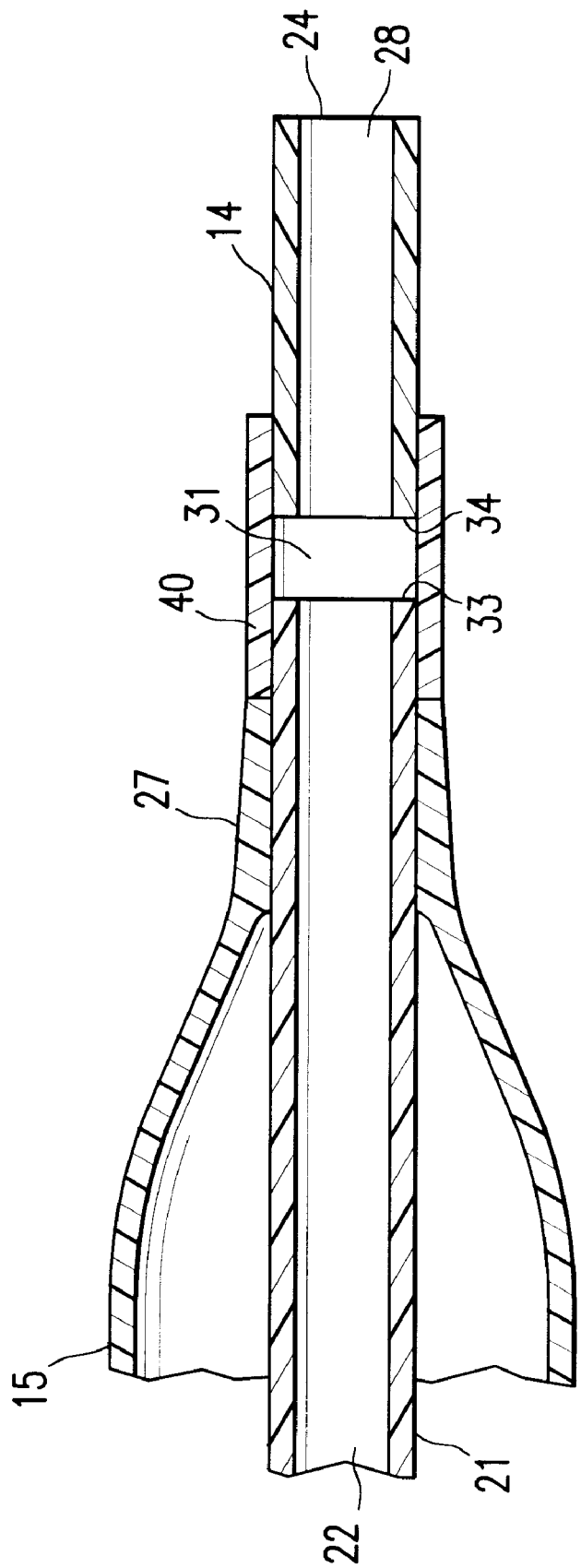
FIG. 8 is an enlarged, longitudinal cross sectional view of an alternate embodiment of the catheter of the invention, having a sheath surrounding the distal end of the catheter and the proximal end of the distal tip.

As best illustrated in FIG. 2, showing an enlarged longitudinal cross sectional view of a distal section of the catheter 10 shown in FIG. 1 taken along lines 2—2, the proximal end of the tip member 14 is spaced distally apart from the distal end of the inner tubular member 21, and thus is not in contact therewith. In the embodiment illustrated in FIG. 2, the distal end of the inner tubular member 21 is disposed distally of the inflatable interior 16 of the balloon. The balloon distal shaft section 27 is disposed about a distal portion of the inner tubular member 21 and a proximal portion of the tip member 14. In a presently preferred embodiment, the balloon distal shaft section 27 is secured to both the distal portion of the inner tubular member 21 and the proximal portion of the tip member 14, as for example, by fusion bonding. It would be obvious to one of ordinary skill in the art that a sheath 40 located distally adjacent to the distal end of the balloon distal shaft section 27 could be disposed about and secured to the inner tubular member 21 or tip member 14 in place of the distal end of the balloon distal shaft section 27.

As best illustrated in FIG. 2, tip member 14 has a lumen 28 in fluid communication with guidewire receiving lumen 22. FIGS. 3, 4 and 5 illustrate transverse cross sectional views from the distal portion of the inner tubular member 21 to the proximal portion of the tip member 14 of the catheter 10, taken along lines 3—3, 4—4, and 5—5, respectively. Tip member 14 is preferably a soft tip formed of a polymeric material which is softer than the material forming at least the distal portion of the inner tubular member 21, which is secured to the balloon distal shaft section 27. The tip member 14 illustrated in FIGS. 2 and 5 is formed of a single layer of a material or a blend of materials. However, the tip member 14 may be a multilayered or multisectioned member (not shown).

In the embodiment illustrated in FIG. 2, a gap 31 is between the distal end of the inner tubular member 21 and the proximal end of the tip member 14. Gap 31 is defined between and in part by a transverse surface 33 of the distal end of the inner tubular member 21 and a transverse surface 34 of the proximal end of the tip member 14. Balloon distal shaft section 27 is in surrounding relation to the distal end of the inner tubular member 21, gap 31, and the proximal end of the tip member 14, so that the balloon distal shaft section 27 extends over and in part defines gap 31. As best illustrated in FIG. 4, showing transverse cross section of the balloon distal shaft section 27 at the gap 31, the inner diameter of the balloon distal shaft section is greater than the inner diameter of the tip member 14.

In an alternative embodiment illustrated in FIG. 6, a portion 32 of the balloon distal shaft section 27 extends between the distal end of the inner tubular member 21 and the proximal end of the tip member 14. The portion 32 is in contact with the transverse surfaces 33 and 34, and has an inner surface 35 which defines a section of the guidewire receiving lumen 22. In the embodiment illustrated in FIG. 6, the inner surface 35 of the portion 32 of the balloon distal shaft section 27 is substantially axially aligned with the inner surface 36 of the tip member 14. The phrase substantially axially aligned should be understood to mean that the portion 32 of the balloon distal shaft section 27 and the tip member 14 have the same inner diameter, or similar inner diameters allowing for some slight variation in the inner surfaces 35/36. In an alternative embodiment, the portion 32 of the balloon distal shaft section 27 may fill only a portion of the space between the inner tubular member 21 and the tip member 14, so that an inner portion of the gap 31 remains (not shown).

In another embodiment illustrated in FIG. 7, intermediate member 41 is secured to and extends between the distal end of the inner tubular member 21 and the proximal end of the tip member 14. In the embodiment illustrated, the intermediate member 41 has a tubular shape with a length equal to the length of the space between the distal end of the inner tubular member 21 and the proximal end of the tip member 14. In a presently preferred embodiment, the intermediate member 41 is formed of a polymeric material which has a Shore Durometer hardness which is lower than a Shore Durometer hardness of the inner tubular member 21 and higher than that of the tip member 14. However, the softness of the material may vary depending on the length of the bond between the balloon distal shaft section 27 and the tip member 14, and the desired use of the catheter 10. The intermediate member 41 can be made from a variety of suitable materials, such as a polyamide including a polyether block amide, and polyethylene based adhesive polymers including ethylene-acrylic acid copolymers such as PRIMACOR sold commercially by Dow Chemical Co., and polyurethanes such as PELLETHANE. The intermediate member 41 may be configured similar to the portion 32 of the balloon distal shaft section 27, as discussed above regarding the embodiment shown in FIG. 6. In the embodiment illustrated in FIG. 7, the intermediate member 41 has an inner surface substantially axially aligned with the inner surface 36 of the tip member 14 and an inner surface of the inner tubular member 21, as discussed above regarding the portion 32 of the balloon distal shaft section 27 shown in FIG. 6. The intermediate member 41, and portion 32 of balloon distal shaft section 27, preferably define annular lumens similar to those shown in FIGS. 3–5.

The space is sufficiently long so that the polymeric materials forming the inner tubular member 21 and tip member 14 do not flow into contact with one another during fusion bonding of the balloon distal shaft section 27 thereto. The length of the space (i.e., the length of gap 31, or portion 32, or intermediate member 41) between the distal end of the inner tubular member 21 and the proximal end of the tip member 14 may vary depending on the desired catheter performance, the length of the balloon distal shaft section 27 and tip member 14, and the method used to bond to tip member. The length of the space is typically about 0.05 mm to about 0.75 mm, more preferably, from about 0.05 mm to about 0.3 mm, preferably about 0.05 mm to about 0.5 mm, most preferably about 0.1 mm to about 0.3 mm. In a presently preferred embodiment, the balloon distal shaft section 27 is about 1 to about 3 mm, preferably about 1.8 to about 2.2 mm. The tip member 14 is typically about 1 to about 5 mm, preferably about 2 to about 3 mm. In the embodiment illustrated in FIGS. 2, 6 and 7, the tip member 14 proximal end is distal to the longitudinal center of the balloon distal shaft section 27. However, in alternative embodiments, the tip member 14 proximal end may be located in various other locations along the length of the balloon distal shaft section 27 (not shown).

The catheter shaft will generally have the dimensions of conventional dilatation or stent deploying catheters. For coronary use, the length of the catheter 10 may be about 90 cm to about 150 cm, and is typically about 145 cm. The outer tubular member 18 has a length of about 15 cm to about 50 cm, an outer diameter (OD) of about 0.03 inch to about 0.05 inch, and an inner diameter (ID) of about 0.031 inch. The inner tubular member 20 has a length of about 15 cm to about 100 cm, an OD of about 0.024 in and an ID of about 0.017 in. The inner and outer tubular members may taper in the distal section to a smaller OD or ID. Although not illustrated, the catheter shaft inner tubular member, or outer tubular member, may be made of multiple shaft sections joined together.

A method of forming a distal tip of a balloon catheter comprises positioning a proximal end of a tip member and a distal end of a catheter shaft within a lumen of a balloon distal shaft section, so that the proximal end of the tip member is distally apart from the distal end of the catheter shaft. The balloon distal shaft section is fusion bonded to the catheter shaft and the tip member by applying heat to at least a portion of the balloon distal shaft section, to form a balloon catheter distal tip having the tip member proximal end fusion bonded to the balloon distal shaft section and spaced distally apart from the distal end of the catheter shaft. Typically a mandrel is positioned within the inner tubular member lumen 22 and the tip member lumen 28 before the fusion bonding. In a presently preferred embodiment, a laser is used to heat the material for fusion bonding, and laser parameters such as focal length and power are selected to provide the desired heat spread. The focal length is typically about 2.6 to about 3.25 inch, and the power is typically about 125 mw to about 170 mw for a YAG (yttrium aluminum garnet) type laser. In one embodiment, the balloon distal shaft section is heated so that the balloon material flows into at least a part of the space between the proximal end of the tip member and the distal end of the catheter shaft. Alternatively, a removable spacer, configured to fit in the space between the inner tubular member and the tip member, may be disposed between the distal end of the inner tubular member 21 and the proximal end of the tip member 14 during fusion bonding, or the fusion bonding heat may be controlled, such that the balloon material does not flow within the space between the inner tubular member 21 and the tip member 14.

In the embodiments illustrated in FIGS. 2, 6 and 7, the outer surface of the balloon distal shaft section tapers distally to a smaller outer diameter. In one embodiment, the taper in the balloon distal shaft section 27 is formed during fusion bonding as the balloon polymeric material is heated and flows distally. Although not shown in the figures, the portion 32 of the balloon distal shaft section 27 may have a dip, i.e., a concave surface, formed as the balloon polymeric material flows into the space between the inner tubular member 27 and the tip member 14.

To the extent not discussed above, the various catheter components may be formed of conventional materials. The inner tubular member may be formed of a variety of conventional catheter shaft materials, including PEBAX, Nylon, and high density polyethylene, used alone or in blends or multilayered members. In a presently preferred embodiment, the inner tubular member includes at least a layer of PEBAX having a Shore Durometer hardness of about 60D to about 72D.

While the present invention is described herein in terms of certain preferred embodiments, those skilled in the art will recognize that various modifications and improvements may be made to the invention without departing from the scope thereof. For example, although discussed primarily in terms of a catheter having an inner and outer tubular member, it would be obvious to one of ordinary skill in the art that the catheter shaft may alternatively have a dual lumen shaft design. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A balloon catheter having a distal end, comprising:
   a) an elongated catheter shaft having a proximal end, a distal end, a proximal shaft section, a distal shaft section, a guidewire receiving lumen extending along at least a distal portion of the catheter shaft to a port at the catheter distal end, and an inflation lumen;
   b) a tip member located at a distal end of the catheter and having a proximal end spaced distally apart from the distal end of the elongated catheter shaft and defining a gap therebetween; and
   c) a balloon on the distal catheter shaft section and having an inflatable interior in fluid communication with the inflation lumen, and a distal balloon shaft section having an extending portion with an interior surface extending longitudinally over the gap and defining at least in part the guidewire receiving lumen.

2. The catheter of claim 1 wherein the balloon inflatable interior is spaced proximal to the distal end of the elongated shaft.

3. The catheter of claim 1, wherein the tip member has a lumen extending therein in fluid communication with a lumen in the elongated shaft.

4. The catheter of claim 1, wherein the tip member is softer than the catheter shaft.

5. The catheter of claim 1, wherein the tip member is formed of a polymeric material having a Shore Durometer hardness lower than a Shore Durometer hardness of a polymeric material forming at least a section of the catheter shaft.

6. The catheter of claim 1, wherein the proximal end of the tip member is spaced apart from the distal end of the catheter shaft by about 0.05 to about 0.3 mm.

7. The balloon catheter of claim 1, including a sheath which is bonded to the catheter shaft and the tip member, and which has a section extending from the distal end of the catheter shaft to the proximal end of the tip member.

8. The balloon catheter of claim 1 wherein the balloon inner surface is bonded to an outer surface of the catheter shaft and an outer surface of the tip member.

9. The balloon catheter of claim 1 wherein the balloon distal shaft section has a tapered outer surface.

10. The balloon catheter of claim 1, wherein the extending portion of the distal balloon shaft section extends between a transverse surface of the distal end of the catheter shaft and a transverse surface of the proximal end of the tip member.

11. The balloon catheter of claim 10, wherein the inner surface of the extending portion of the balloon distal shaft section is substantially axially aligned with an inner surface of the tip member.

12. The balloon catheter of claim 1 wherein the catheter shaft comprises an outer tubular member defining the inflation lumen and an inner tubular member disposed within at least a portion of the outer tubular member and defining the guidewire lumen, wherein the distal end of the inner tubular member is spaced apart from the proximal end of the tip member.

13. The balloon catheter of claim 12 wherein the distal balloon shaft section is secured to the inner tubular member.

14. A balloon catheter, comprising:
  a) an elongated catheter shaft having a proximal end, a distal end, an outer tubular member defining an inflation lumen, and an inner tubular member having a distal end and disposed within at least a section of the outer tubular member and defining a guidewire lumen;
  b) a tip member located at the distal end of the catheter and having a proximal end spaced distally apart from the distal end of the inner tubular member and defining a gap therebetween; and
  c) a balloon on the distal catheter shaft section and having an inflatable interior in fluid communication with the inflation lumen, and a distal balloon shaft section having an extending portion with an interior surface extending longitudinally over the gap and defining at least in part the guidewire receiving lumen.

* * * * *

UNITED STATES PATENT AND TRADEMARK OFFICE
CERTIFICATE OF CORRECTION

PATENT NO. : 6,368,301 B1
DATED : April 9, 2002
INVENTOR(S) : Rasean L. Hamilton It is certified that error appears in the above-identified patent and that said Letters Patent is hereby corrected as shown below:

Column 4,
Lines 58 and 59, delete "more preferably, from about 0.05 mm to about 0.3 mm," and add that statement at line 59 after "0.5 mm,".

Signed and Sealed this

Thirty-first Day of December, 2002

JAMES E. ROGAN
*Director of the United States Patent and Trademark Office*